US011709877B2

(12) United States Patent
Barkan et al.

(10) Patent No.: US 11,709,877 B2
(45) Date of Patent: Jul. 25, 2023

(54) SYSTEMS AND METHODS FOR TARGETED ANNOTATION OF DATA

(71) Applicant: International Business Machines Corporation, Armonk, NY (US)

(72) Inventors: Ella Barkan, Haifa (IL); Aviad Zlotnick, Mitzpeh Netofah (IL)

(73) Assignee: International Business Machines Corporation, Armonk, NY (US)

( * ) Notice: Subject to any disclaimer, the term of this patent is extended or adjusted under 35 U.S.C. 154(b) by 580 days.

(21) Appl. No.: 16/746,993

(22) Filed: Jan. 20, 2020

(65) Prior Publication Data
US 2021/0225466 A1      Jul. 22, 2021

(51) Int. Cl.
  *G06F 16/00*        (2019.01)
  *G06F 16/35*        (2019.01)
  (Continued)

(52) U.S. Cl.
  CPC .......... *G06F 16/35* (2019.01); *G06F 16/9535* (2019.01); *G06F 16/9538* (2019.01);
  (Continued)

(58) Field of Classification Search
  None
  See application file for complete search history.

(56) References Cited

U.S. PATENT DOCUMENTS 7,849,030 B2 * 12/2010 Ellingsworth ........ G06F 16/353
                                                706/20
8,751,495 B2 *  6/2014 Chung .................. G16H 50/70
                                                707/802
(Continued)

FOREIGN PATENT DOCUMENTS

WO      WO2020117869 A1 *  6/2020

OTHER PUBLICATIONS

Khan et al., "Text Mining Challenges and Applications, A Comprehensive Review"; IJCNS, 2020.*
(Continued)

*Primary Examiner* — Daniel A Kuddus
(74) *Attorney, Agent, or Firm* — G.E. Ehrlich Ltd.

(57) ABSTRACT

There is provided a system and a method of generating an annotated structured dataset, comprising: receiving a medical classification term, searching over the unstructured patient data for extracting unclassified unstructured text fragments, presenting a subset of the unclassified unstructured text fragments, receiving an indication of a selection of none or at least one of the text fragments, and one of: (i) classifying non-selected unclassified unstructured text fragments according to the medical classification term, and classifying selected text fragments as not satisfying the medical classification term, and (ii) classifying selected unclassified unstructured text fragments according to the medical classification term, and classifying non-selected unclassified unstructured text fragments as not satisfying the medical classification term, and iterating the searching, and/or the presenting, until no text fragments are obtained by the search, wherein the annotated structured dataset is created by the classification of unclassified unstructured text fragments into the medical classification term.

20 Claims, 5 Drawing Sheets

(51) Int. Cl.
*G16H 10/60* (2018.01)
*G06F 16/9538* (2019.01)
*G06F 40/211* (2020.01)
*G06F 16/9535* (2019.01)
*G06F 18/214* (2023.01)

(52) U.S. Cl.
CPC .......... *G06F 18/214* (2023.01); *G06F 40/211* (2020.01); *G16H 10/60* (2018.01)

(56) References Cited

U.S. PATENT DOCUMENTS

| | | | | |
|---|---|---|---|---|
| 9,734,297 | B2* | 8/2017 | Syeda-Mahmood | G16H 50/70 |
| 10,593,423 | B2* | 3/2020 | Baldwin | G06F 16/3329 |
| 10,957,433 | B2* | 3/2021 | Lucas | G16H 10/60 |
| 10,977,292 | B2* | 4/2021 | Eifert | G16H 70/00 |
| 11,068,490 | B2* | 7/2021 | Eifert | G06F 16/93 |
| 11,069,432 | B2* | 7/2021 | Guo | G16H 50/20 |
| 2004/0064438 | A1* | 4/2004 | Kostoff | G06F 16/35 |
| 2004/0243554 | A1* | 12/2004 | Broder | G06F 16/38 |
| 2007/0112763 | A1* | 5/2007 | Broder | G06F 16/334 |
| | | | | 707/999.005 |
| 2007/0282824 | A1* | 12/2007 | Ellingsworth | G06F 16/313 |
| | | | | 707/999.005 |
| 2011/0078145 | A1* | 3/2011 | Chung | G16H 50/70 |
| | | | | 707/E17.046 |
| 2013/0226743 | A1* | 8/2013 | Kundu | G06F 16/54 |
| | | | | 705/27.2 |
| 2013/0226843 | A1* | 8/2013 | Syeda-Mahmood | G16Z 99/00 |
| | | | | 706/12 |
| 2014/0222443 | A1* | 8/2014 | Danenberg | C12Q 1/6886 |
| | | | | 705/2 |
| 2015/0006199 | A1* | 1/2015 | Snider | G16H 50/20 |
| | | | | 705/3 |
| 2015/0356057 | A1* | 12/2015 | Subramanian | G06F 40/10 |
| | | | | 704/9 |
| 2016/0019299 | A1* | 1/2016 | Boloor | G06F 16/9535 |
| | | | | 705/3 |
| 2017/0193085 | A1* | 7/2017 | Boguraev | G06F 40/284 |
| 2018/0107801 | A1* | 4/2018 | Guo | G16H 15/00 |
| 2018/0232489 | A1* | 8/2018 | Fink | G16H 50/70 |
| 2019/0206524 | A1* | 7/2019 | Baldwin | G16H 50/70 |
| 2020/0226164 | A1* | 7/2020 | Eifert | G06F 16/3334 |

OTHER PUBLICATIONS

Hauer et al., Data and Information Leakage Prevention Within the Scope of Information Security; IEEE 2015.*

* cited by examiner

SYSTEMS AND METHODS FOR TARGETED ANNOTATION OF DATA

BACKGROUND

The present invention, in some embodiments thereof, relates to annotation of data and, more specifically, but not exclusively, to systems and methods for targeted annotation of data.

Annotation for training data for artificial intelligence (AI) applications affects performance of the AI model, but the annotation is extremely slow, expensive, and prone to error. For example, annotation of records of patients participating in a clinical trial is a time consuming and tedious task. Using manual methods, annotators manually review each health record of each patient, and manually labeling different portions of the health record with labels corresponding to medical concepts of the clinical trial.

SUMMARY

According to a first aspect, a system for generating an annotated structured dataset from unstructured patient data of a plurality of patients, comprises: at least one hardware processor executing a code for: receiving a medical classification term for classification of the unstructured patient data, searching, via a search engine, over a sample of the unstructured patient data using the medical classification term, for extracting a plurality of unclassified unstructured text fragments, presenting on a display, a subset of the plurality of unclassified unstructured text fragments, receiving from a user, an indication of a selection of none or at least one of the plurality of unclassified unstructured text fragments, and one of: (i) classifying non-selected unclassified unstructured text fragments according to the medical classification term, and classifying selected unclassified unstructured text fragments as not satisfying the medical classification term, and (ii) classifying selected unclassified unstructured text fragments according to the medical classification term, and classifying non-selected unclassified unstructured text fragments as not satisfying the medical classification term, and iterating the searching, and/or the presenting of the subset, until no unclassified unstructured text fragments are obtained by the search engine, wherein the annotated structured dataset is created by the classification of unclassified unstructured text fragments into the medical classification term.

According to a second aspect, a method of generating an annotated structured dataset from unstructured patient data of a plurality of patients, comprises: receiving a medical classification term for classification of the unstructured patient data, searching, via a search engine, over a sample of the unstructured patient data using the medical classification term, for extracting a plurality of unclassified unstructured text fragments, presenting on a display, a subset of the plurality of unclassified unstructured text fragments, receiving from a user, an indication of a selection of none or at least one of the plurality of unclassified unstructured text fragments, and one of: (i) classifying non-selected unclassified unstructured text fragments according to the medical classification term, and classifying selected unclassified unstructured text fragments as not satisfying the medical classification term, and (ii) classifying selected unclassified unstructured text fragments according to the medical classification term, and classifying non-selected unclassified unstructured text fragments as not satisfying the medical classification term, and iterating the searching, and/or the presenting of the subset, until no unclassified unstructured text fragments are obtained by the search engine, wherein the annotated structured dataset is created by the classification of unclassified unstructured text fragments into the medical classification term.

According to a third aspect, a computer program product for generating an annotated structured dataset from unstructured patient data of a plurality of patients, comprises: a non-transitory memory storing thereon code for execution by at least one hardware process, the code including instructions for: receiving a medical classification term for classification of the unstructured patient data, searching, via a search engine, over a sample of the unstructured patient data using the medical classification term, for extracting a plurality of unclassified unstructured text fragments, presenting on a display, a subset of the plurality of unclassified unstructured text fragments, receiving from a user, an indication of a selection of none or at least one of the plurality of unclassified unstructured text fragments, and one of: (i) classifying non-selected unclassified unstructured text fragments according to the medical classification term, and classifying selected unclassified unstructured text fragments as not satisfying the medical classification term, and (ii) classifying selected unclassified unstructured text fragments according to the medical classification term, and classifying non-selected unclassified unstructured text fragments as not satisfying the medical classification term, and iterating the searching, and/or the presenting of the subset, until no unclassified unstructured text fragments are obtained by the search engine, wherein the annotated structured dataset is created by the classification of unclassified unstructured text fragments into the medical classification term.

In a further implementation form of the first, second, and third aspects, the selection of the indication of at least one of the subsets of the plurality of unstructured text fragments for exclusion or inclusion is performed using a single click, via a GUI presenting the subset of the plurality of unclassified unstructured text fragments. In a further implementation form of the first, second, and third aspects, the search engine comprises a trained model trained on a training dataset of labelled data, and the trained search engine is updated during each iteration by being fed an indication of the plurality of classified and/or unclassified unstructured text fragments.

In a further implementation form of the first, second, and third aspects, each iteratively presented subset is obtained by executing the search engine on another sample of the unstructured patient data.

In a further implementation form of the first, second, and third aspects, during each iteration, the search engine extracts unique unclassified unstructured text fragments that have not been extracted in a previous iteration.

In a further implementation form of the first, second, and third aspects, during each iteration, all instances of the unclassified unstructured text fragments in a corpus of the unstructured patient data are classified according to the respective medical classification term.

In a further implementation form of the first, second, and third aspects, further comprising: obtaining a plurality of candidate sub-classification terms potentially semantically related to the medical classification term, presenting on a display, a subset of the plurality of candidate sub-classification terms, receiving, from a user, a selection of at least one of the plurality of candidate sub-classification terms for inclusion in a modified search set, iterating the obtaining and/or the presenting until all of the plurality of candidate sub-classification terms have been obtained and presented, and wherein the search engine searches over the sample of the unstructured patient data using the modified search set.

In a further implementation form of the first, second, and third aspects, the selection of the at least one of the plurality of candidate sub-classification terms is for exclusion from the modified search set, and is performed using a single click, via a GUI presenting the cluster of the subset of the plurality of candidate sub-classification terms.

In a further implementation form of the first, second, and third aspects, the plurality of candidate sub-classification terms are extracted from unstructured clinical data by natural language processes (NLP) that are designed and trained to extract terms and phrases that are synthetically similar to an input term or phrase.

In a further implementation form of the first, second, and third aspects, the unstructured patient data includes at least one member of the group consisting of:

physician manually written notes, and transcribed dictations.

In a further implementation form of the first, second, and third aspects, the unstructured patient data is created by a plurality of different healthcare providers using different terminology that has a semantically similar meaning.

In a further implementation form of the first, second, and third aspects, a number of members of the subset of the plurality of unclassified unstructured text fragments simultaneously respectively presented within a GUI is selected according to screen parameters of a display presenting the GUI.

In a further implementation form of the first, second, and third aspects, further comprising selecting the subset of the plurality of unclassified unstructured text fragments for presentation according to a statistical similarity value, wherein unclassified unstructured text fragments of the subset have a higher statistical similar value in comparison to non-selected unclassified unstructured text fragments excluded from the subset.

In a further implementation form of the first, second, and third aspects, further comprising selecting the subset of the plurality of unclassified unstructured text fragments of a current iteration according to a statistical similarity value computed relative to unclassified unstructured text fragments selected from the subset of a previous iteration.

In a further implementation form of the first, second, and third aspects, the subset is selected according to a requirement of the statistical similarity value denoting similarity to the previous iteration.

In a further implementation form of the first, second, and third aspects, the subset is selected according to a requirement of the statistical similarity value denoting dis-similarity to at least one indication of the subset of the plurality of unclassified unstructured text fragments selected for exclusion in a previous iteration.

In a further implementation form of the first, second, and third aspects, the medical classification term is based on clinical data, and the unstructured patient data is of medical records of the patients.

In a further implementation form of the first, second, and third aspects, the medical classification term is one medical classification term selected from a plurality of medical classification terms, and the code is iterated for each of the plurality of medical classification terms, and wherein the annotated dataset includes at least one of the plurality of medical classification terms classifying unstructured data fragments of patient data for each of the plurality of patients.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

The present invention, in some embodiments thereof, relates to annotation of data and, more specifically, but not exclusively, to systems and methods for targeted annotation of data.

An aspect of some embodiments of a present invention, relates to systems, methods, an apparatus, and/or code instructions (i.e., stored on a data storage device, executable by one or more hardware processors) for generating an annotated structured dataset from unstructured patient data of patients.

A search engine searches over at least a sample of the unstructured patient data using a medical classification term for classification of the unstructured patient data. The search engine extracts unclassified unstructured text fragments (i.e., unclassified with respect to the current search term). A subset of the unclassified unstructured text fragments is presented on a display, for example, within a user interface, optionally a graphical user interface (GUI). The number of presented unclassified unstructured text fragments in the subset presented simultaneously on the display may vary according to screen parameters, such as available screen space. An indication of a selection of none or at least one of the unclassified unstructured text fragments is received, for example, the user clicking on the text fragments. In one implementation, non-selected unclassified unstructured text fragments are classified according to the medical classification term, and selected unclassified unstructured text fragments are classified as not satisfying the medical classification term. In such an implementation, the user selects the 'odd ones out', i.e., the fragments which are not to be classified according to the medical classification term. Assuming the search engine is correct most of the time, selecting the 'odd ones out' is expected to reduce the number of selection actions (e.g., click per selected fragment) in comparison to selecting the fragments that are correctly retrieved and classified according to the medical classification term. In an alternative implementation, selected unclassified unstructured text fragments are classified according to the medical classification term, and non-selected unclassified unstructured text fragments are classified as not satisfying the medical classification term. The searching, and/or the presenting of the subset of retrieved unclassified unstructured text fragments is iterated until no unclassified unstructured text fragments obtained by the search engine remain (i.e., all unstructured text fragments have been classified into the medical classification category, or have been identified as not to be classified into the medical classification category). The annotated structured dataset is created by the classification of unclassified unstructured text fragments into the medical classification term. The process is iterated for each medical classification term, optionally one medical classification term at a time. The single medical classification term may include a search set of semantically similar terms with common meaning.

Optionally, the annotated dataset is used as a training dataset for training an artificial intelligence model (e.g., neural network, statistical classifier), for example, for classifying previously unseen unstructured text fragments of previously unseen patient data into one or more of the medical classification terms. In another implementation, the annotated dataset is used by another model to extract and/or process data, for example, to analyze results of a clinical trial, by extracting values from the annotated dataset according to medical classification terms.

Optionally, each presented subset is iteratively obtained by re-executing the search engine on another part of the unstructured patient data that has not yet been searched. The search engine may be implemented as a trained model that is trained on a training dataset of labelled data. The trained search engine may be updated during each iteration by being fed an indication of the classified and/or unclassified unstructured text fragments.

At least some implementations of the systems, methods, apparatus, and/or code instructions described herein improve interaction of a user performing annotation of unstructured patient data with a computer used, for generating an annotated structured dataset. By presenting a subset of unclassified unstructured text fragments found in response to searching with a single medical classification term, the user is shown small amounts of data to annotate at a time, which are expected to fall within the same context (of the medical classification term). The process for classifying the presented unstructured text fragments is simplified, as the user clicks on the 'odd one out', rather than selecting what is expected to be a much larger dataset of relevant text fragments for classification. For example, using a single click, the user may select the unstructured text fragment which is unrelated to the medical classification term. The single click may occur when the user clicks on an icon denoting an acceptance of all presented fragments, i.e., without exclusion of an of the displayed fragments. Such single slick denoting acceptance of all presented fragments may be expected to occur for a majority of the presented subsets of simultaneously presented fragments, for example, when the accuracy of retrieval by the search engine is high, optionally when the search engine is iteratively updated, as described herein. Alternatively, more than a single click may occur, for example, two (or more clicks), such as a click per selected fragment, and another click to indicate completion of the selection. The process is iterated, each time presenting to the user a small batch of unstructured text fragments for classification, optionally until all text fragments have been classified into the medical classification term or not. For example, about 3-15, or about 7-10 or other number of text fragments are presented simultaneously, optionally according to the amount of space available on the display. The process is iterated for each medical classification term, one medical classification term at a time, optionally until all medical classification terms have been used to classify the unstructured patient data.

At least some implementations of the systems, methods, apparatus, and/or code instructions described herein provide the user with an interface for performing multiple partial annotations, in contrast for example, to performing complete annotations.

At least some implementations of the systems, methods, apparatus, and/or code instructions described herein relate to the technical problem of improving efficiency of annotating unstructured patient data, for example, health records of patients participating in a clinical trial. Annotated dataset have a wide range of usages, for example, for training a machine learning model. The annotation process, which is traditionally done manually, is time consuming, expensive, and requires specialized annotators with medical knowledge. The trained experts read through each unstructured document (e.g., of each health record), understand the documents, and may enter extracted information into a user interface and/or use other methods to annotate the records. The annotation process is challenging for several reasons:

(i) The huge quantity of data, for example, for thousands of patients, where data for each patient (e.g., each health record) may contain dozens of documents (e.g., medical reports and/or test results).

(ii) Multiple different annotations for the same patient data (e.g., for each health record), sometimes for the same portion of text. Performing multiple mental context switches is difficult for a human, and is error prone.

(iii) Different terminology used by different users that provided the unstructured patient data (e.g., documents of the health records). For example, physicians of different specialties, different medical training levels, and other healthcare provides (e.g., nurses, physical therapy, pharmacy). Different users, or even the same user, may use different terms that mean the same thing, or relate to the same concept, for example, hormonal treatment and estrogen may both relate to the concept of hormone replacement therapy. Moreover, the same medical terminology may refer to different contexts which are unrelated, for example, hormonal treatment of cancer, and hormone replacement therapy for post-menopausal women.

(iv) Machine learning methods still require a very large number of annotated samples, and are still prone to error for example, due to the problems in terminology described in (iii). Therefore, even using machine learning methods cannot escape a requirement for a large amount of human effort for manual annotation.

(v) The data is unstructured, making it more difficult to annotate correctly. For example, a single sentence may be divided into different parts, where each part has one or more different annotations assigned to it. Incorrect division of the sentence may lead to an inability or a difficulty in assigning annotations.

At least some implementations of the systems, methods, apparatus, and/or code instructions described herein improve the technology of annotation of data for creating structured datasets for training an AI model. In at least some implementations the improvement is obtained by reducing the number of user interface operations for extracting information from clinical records by presenting similar results of a single topic, and/or reduces error in the annotated dataset and/or improves computational efficiency and/or accuracy of the annotated dataset and/or reduces false positives.

At least some implementations of the systems, methods, apparatus, and/or code instructions described herein improve over existing methods of extracting data from medical documents. None of the exiting methods relate to improving interaction of a user with a computer for annotating of unstructured data, by iterative presentation of subsets of fragments extracted from the unstructured data according to a single medical classification term at a time (or a set of terms semantically similar to the medical classification term), and for selection by the user, optionally for exclusion from classification. For example, some existing processes are only based on a user correcting a model that extracts medical facts from a text by identifying a fact that should be associated with the extracted text, but is not. However, since the model itself is trained using manually annotated data the above described problems with generating the annotated dataset are encountered. Moreover, the model itself cannot perform annotation. In another example, some processes are designed to perform a semantic search for related clinical concepts based on semantic meaning, which are difficult to manually evaluate for correctness and difficult to use for annotation of unstructured data. In yet another example, other processes perform natural language processing of free text based on domain specific knowledge, which are difficult to manually evaluate for correctness and difficult to use for annotation of unstructured data. In yet another example, clustering of clinically relevant medical concepts is performed, which is difficult to manually evaluate for correctness and difficult to use for annotation of unstructured data. In yet another example, other methods are based on natural language processing for mining of patient data, which are difficult to manually evaluate for correctness and difficult to use for annotation of unstructured data. In yet another example, other methods are based on extracting data elements deemed as relevant according to clinical guidelines, which are difficult to manually evaluate for correctness and difficult to use for annotation of unstructured data. In yet another example, other methods are based on identifying and extracting medical conditions and supporting evidences from electronic health records, which are difficult to manually evaluate for correctness and difficult to use for annotation of unstructured data. In yet another example, other methods are based on mapping clinical terminology with natural language processing, which are difficult to manually evaluate for correctness and difficult to use for annotation of unstructured data.

Improvements over existing processes provided by at least some implementations of the systems, methods, apparatus, and/or code instructions described herein include one or more of:

(i) Presenting a single type of information at a time, for example, the presented subset of results (e.g., within a GUI) are obtained for a single medical classification term, or a set of terms that are semantically similar to the single medical classification term. The single type of information at a time reduces mental context switches and enables the annotating user to focus on one concept at a time.

(ii) The subset of presented results (e.g., within the GUI) during each iteration may be approved by a single selection gesture, for example, a single click, to exclude one erroneous result, or to approve all results. The results presented may be homogenous to one another, reducing effort of approving all results. The homogeny may be increased, for example, by selecting results that are similar to one another, similar to results in a previous iteration, and/or are dissimilar to previously rejected records.

(iii) Iteratively performing multiple partial annotations of small chunks of data for iteratively training the search engine, optionally until the trained search engine converges to a target accuracy of correctly extracting the unstructured text fragments.

(iv) Analyzing and/or evaluating text fragments, such as for classification by the medical classification term, is different than analyzing and/or evaluating images stemming from different challenges of the different modalities.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
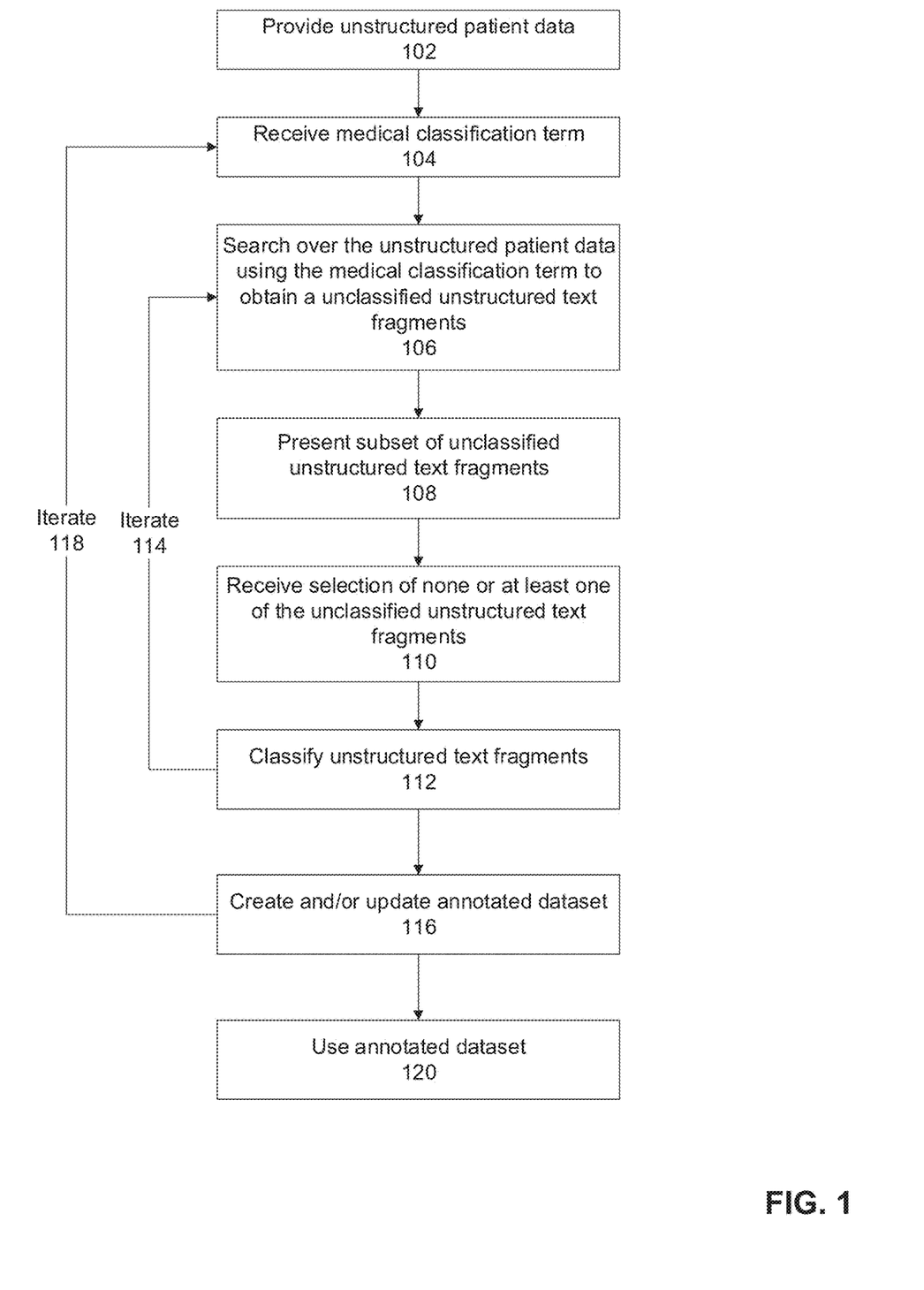
FIG. 1 is a flowchart of a method for generating an annotated structured dataset from unstructured patient data of multiple patients, in accordance with some embodiments of the present invention.
Figure 2:
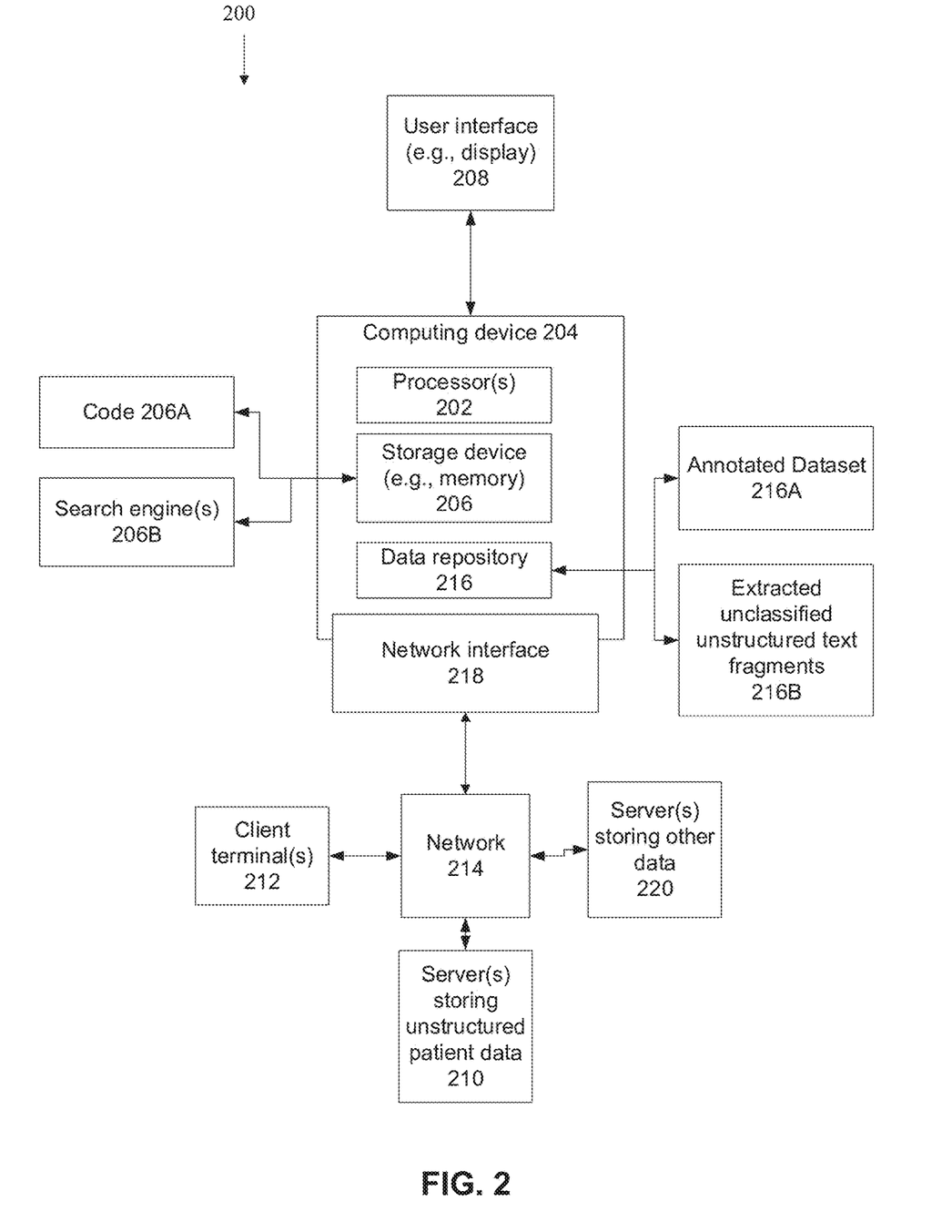
FIG. 2 is a block diagram of a system for generating an annotated structured dataset from unstructured patient data of multiple patients, in accordance with some embodiments of the present invention.

Reference is now made to FIG. 1, which is a flowchart of a method for generating an annotated structured dataset from unstructured patient data of multiple patients, in accordance with some embodiments of the present invention. Reference is also made to FIG. 2, which is a block diagram of a system for generating an annotated structured dataset from unstructured patient data of multiple patients, in accordance with some embodiments of the present invention. System 200 may implement the acts of the method described with reference to FIG. 1, by processor(s) 202 of a computing device 204 executing code instructions 206A and/or 206B stored in a storage device 206 (also referred to as a memory and/or program store).

Computing device 204 may be implemented as, for example, a client terminal, a server, a computing cloud, a virtual server, a virtual machine, a mobile device, a desktop computer, a thin client, a Smartphone, a Tablet computer, a laptop computer, a wearable computer, glasses computer, and a watch computer.

Multiple architectures of system 200 based on computing device 204 may be implemented. In an exemplary implementation, computing device 204 storing code 206A and/or 206B, may be implemented as one or more servers (e.g., network server, web server, a computing cloud, a virtual server) that provides services (e.g., one or more of the acts described with reference to FIG. 1) to one or more client terminals 212 over a network 214, for example, providing software as a service (SaaS) to the client terminal(s) 212, providing software services accessible using a software interface (e.g., application programming interface (API), software development king (SDK)), providing an application for local download to the client terminal(s) 212, and/or providing functions using a remote access session to the client terminals 212, such as through a web browser. For example, users having client terminals 212 installed in their offices (or using mobile devices) use their local client terminals to access computing device 204, which may be remotely located. Computing device 204 generates instructions for presentation of the UI that is iteratively updated and/or creates the annotated dataset, as described herein. In another implementation, computing device 204 may include locally stored software (e.g., code 206A and/or 206B) that performs one or more of the acts described with reference to FIG. 1, for example, as a self-contained client terminal. In another example, client terminals 212 may obtain the created annotated dataset 216A from computing device 204 (which may create the annotated dataset 216A using code 206A and/or 206B as described herein) for local installation and use. Each client terminal 212 may store its own annotated dataset 216A, which may be custom created according to its own clinical trial data and/or designated patient health records.

Processor(s) 202 of computing device 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include a single processor, or multiple processors (homogenous or heterogeneous) arranged for parallel processing, as clusters and/or as one or more multi core processing devices.

Data storage device 206 stores code instructions executable by processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Storage device 206 stores code 206A that implements one or more features and/or acts of the method described with reference to FIG. 1 when executed by processor(s) 202. Storage device 206 may store search engine code 206B that searches unstructured data for extraction of data, as described herein.

Computing device 204 may include a data repository 216 for storing data, for example, annotated dataset 216A, as described herein, and/or unclassified unstructured text fragments 216B extracted from the unstructured patient data by the search engine, as described herein. Data repository 216 may be implemented as, for example, a memory, a local hard-drive, virtual storage, a removable storage unit, an optical disk, a storage device, and/or as a remote server and/or computing cloud (e.g., accessed using a network connection).

Network 214 may be implemented as, for example, the internet, a local area network, a virtual private network, a wireless network, a cellular network, a local bus, a point to point link (e.g., wired), and/or combinations of the aforementioned.

Computing device 204 may include a network interface 218 for connecting to network 214, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may connect using network 214 (or another communication channel, such as through a direct link (e.g., cable, wireless) and/or indirect link (e.g., via an intermediary computing unit such as a server, and/or via a storage device) with one or more of:

Server(s) 210 storing unstructured patient data (e.g., patient medical records), as described herein.

Client terminal(s) 212, which may be used by users remotely accessing computing device 204, as described herein.

Server(s) 220 storing other data, optionally including unstructured data, for example, used to obtain medical classification terms, and/or sub-classification terms, as described herein.

Computing device 204 and/or client terminal(s) 212 include and/or are in communication with one or more physical user interfaces 208 that include a mechanism for presenting the UI (e.g., GUI) described herein. Exemplary user interfaces 208 include, for example, one or more of, a touchscreen, a display, a keyboard, a mouse, and voice activated software using speakers and microphone.

Referring now back to FIG. 1, at 102, unstructured patient data is provided (e.g., accessed, received).

The unstructured patient data may be stored, for example, as patient medical records, and/or other data associated with the patient that is not necessarily stored in the patient medical record. The unstructured patient may be stored in a central database, a distributed database, and/or as a collection of datasets (e.g., files) which may be stored on one or more memories of one or more computing devices.

The unstructured patient data may include, for example, text, sentences, words, paragraphs, optionally with associated values such as numerical values (e.g., blood test results), and/or codes (e.g., diagnostic codes). Audio files may be transcribed into text by manual and/or automated processes.

The unstructured patient data may be created by multiple different users, such as different healthcare provides, for example, doctors, specialists of different fields, medical residents, medical students, nurses, physiotherapists, and pharmacists. The different healthcare provides may use different terminology and/or phrases that have a semantically similar meaning. At least some of the systems, methods, apparatus, and/or code instructions described herein are designed for improving the interaction of a user with a computer for annotating the different phrases with different terminology under a single common medical classification term.

The unstructured patient data may include physicians' manually written notes (e.g., typed, hand notes which may be scanned and/or converted into text using optical character recognition) and/or transcribed dictations (e.g., manually and/or automatically transcribed from audio files), for example, radiology reports, daily patient evaluation reports (subject, objective, assessment, plan (SOAP)) made by members of the healthcare team, specialist visit summary (e.g., physician, occupational therapy, physical therapy), and notes made during patient visits to a primary care practitioner.

At 104, a medical classification term for classification of the unstructured patient data is received.

Optionally, multiple medical classification terms are received. In such a case, one medical classification term may be implemented at a time, as described herein.

The medical classification term may be received, for example, manually entered by a user, manually selected by a user from a list of medical classification terms, predefined by a dictionary, predefined by the Unified Medical Language System (UMLS) and/or automatically extracted by code from the unstructured patient data and/or from other sources (e.g., by natural language processes (NLP) that are designed and trained to extract medical classification terms).

In one example, the medical classification term is based on clinical data, optionally collected from a clinical trial, and the unstructured patient data is of medical records of the patients participating in the clinical trial.

Clinical terms may be obtained, for example, from the SNOMED dataset, accessible at http://www(dot)snomed (dot)org. Unstructured data may be obtained, for example, from electronic medical records (EMR) of patients.

Each medical classification term may be selected to focus on one type of information at a time, for example, "Has hormone replacement therapy been used" using the term "hormone replacement therapy", or "has a BRCA mutation been detected" using the term "BRCA".

At 106, the medical classification term is fed into a search engine that searches over at least a sample of the unstructured patient data. The search may be performed iteratively over different portions of the unstructured patient data, such that at each iteration a new previously unsearched portion is searched. Alternatively, the search is performed over the entire corpus of unstructured patient data.

The search engine returns a set of unclassified unstructured text fragments extracted from the unstructured patient data.

Optionally, a search set is created based on the medical classification term. The search set includes multiple terms that are semantically similar to the medical classification term, such that text fragments found by a search engine searching using the search set are potentially classified into the same medical classification term. For example, the search set represents variations of medical terms having a common meaning, and/or different phrases used by different specialists to describe the same thing. Additional details of an exemplary process of creating the search set is described with reference to FIG. 3.

At 108, a subset of the unclassified unstructured text fragments is simultaneously presented on a display. The display of the subset, rather than the entire set of unclassified unstructured fragments, helps the user interact with the computer for annotating of the subset, by reducing the amount of simultaneously presented data requiring the user's attention. Moreover, since the subset is extracted from a single medical classification term, the focus of the user is improved by the common context of the presented subset.

The subset of unclassified unstructured text fragments may be presented within a user interface, optionally a GUI. For example, using a table, where each cell of the table presents a single unclassified unstructured text fragment. The table may be of a single column with multiple rows, or multiple columns with multiple rows, or multiple columns with single row.

Optionally, a number of the member of the subset of unclassified unstructured text fragments simultaneously respectively presented on the display (e.g., within the GUI) is selected according to screen parameters of a display presenting the subset (e.g., the GUI), for example, dimension of the screen, resolution of the screen, dimensions of a window of the screen within which the subset is presented. The number may be based on the number and/or arrangement of cells of the table presenting the subset. For example, using a small screen such as on a mobile device (e.g., smartphone, smartwatch), a smaller number is presented, optionally using a smaller table. In another example, using a large high resolution monitor, a larger number of text fragments may be simultaneously presented. Alternatively or additionally, the user may select parameters for the number, for example, defining the size of the font used to present the text fragments, selecting the number directly, and/or setting the dimensions of the table. The number of members of the subset may be selected as a reasonable number for a human to simultaneously visually inspect without being overwhelmed and/or optimized for accurate performance, for example, based on experiments. The number of members of the subset may be, for example, between 3-10, or 7-11, or 4-15, or 5-8, or other ranges and/or other numbers.

Optionally, members of the subset may be selected to be homogenous to one another. The more homogenous the display, the easier it may be for the user to visually detect and select the incorrect result. Homogeneity of the display may be increased by selecting fragments that are similar to each other (in the current iteration), similar to previously accepted fragments (in a previous iteration), dissimilar to previously rejected fragments (in a previous iteration), and/or a combination of the above.

Optionally, members of the subset are selected from the corpus of extracted unclassified unstructured text fragment (obtained by the search engine) for presentation according to a statistical similarity value that is higher in comparison to non-selected unclassified unstructured text fragments excluded from the subset. In other words, members of the subset are more similar to each other (according to the statistical similarity value) in comparison to fragments not included in the subset.

Similarity may be computed using an existing document similarity process, for example, as described with reference to US2019/0102380, and/or as described with reference to Chen Ye, Daniel Fabbri, "*Extracting similar terms from multiple EMR-based semantic embeddings to support chart reviews*", Journal of Biomedical Informatics, Volume 83 July 2018, Pages 63-72, all of which are incorporated herein by reference in their entirety.

Alternatively or additionally, members of the subset of a current iteration (i.e., for current simultaneous presentation on the display) are selected according to a requirement of a statistical similarity value computed relative to unclassified unstructured text fragments of a subset of a previous iteration (i.e., which were previously presented on the display during a previous iteration). The requirement may denote similarity to the previous iteration computed according to the statistical similarity value, where fragments that are similar to previously presented fragments are selected. The requirement may define similarity to the fragments of the previously presented subset that were selected by the user during the previous iteration. Alternatively, the requirement may define similarity to the fragments of the previously presented subset that were non-selected by the user during the previous iteration. The selection by the user may denote exclusion from classification using the medical term, or alternatively the selection by the user may denote classification using the classification term. For example, text fragments having a statistical similarity value above a threshold with respect to the set of fragments previously presented but non-selected by the user are selected, where non-selected fragments are classified according to the medical classification term.

Alternatively or additionally, members of the subset of a current iteration are selected according to a requirement of the statistical similarity value denoting dis-similarity to one or more members of the subset selected by the user (for classification, or alternatively to exclude from classification) in a previous iteration. For example, the members for the current iteration that are most different than members of the subset of the previous iteration that were selected (or not selected) by the user are presented.

At 110, an indication of a selection of none or at least one of the unclassified unstructured text fragments is received from a user.

In one implementation, the selection denotes text fragments to exclude from classification with the medical classification term. Alternatively, in another implementation, the selection denotes text fragments to include, i.e., to classify using the medical classification term. The decision of whether selected fragments are included or excluded may be, for example, based on minimizing the number of gestures to perform. The default may be selection for exclusion, based on the assumption that the search engine is mostly correct, where most of the presented fragments of the subset are correctly retrieved and should be classified, and the selected fragments (which are minority) are incorrectly retrieved and should not be classified.

The selection may be performed using a single user gesture, for example, a single click (e.g., using a mouse cursor), a single tap on a touch screen, and/or a single audio command. Each text fragment may be independently selected using the single gesture. The single gesture may be provided via the GUI presenting the subset, for example, clicking on individual cells within the GUI. When multiple fragment selections are made, the user may select each fragment with a single click, followed by another indication denoting completion of the selections, for example, clicking on a 'completed' icon, and/or saying "completed" into a microphone which is processed by voice recognition code. In another example, the single gesture may include selection of an icon (e.g., button) denoting an acceptance of all but the marked (i.e., use selected) fragments. In yet another example, the single gesture may include selection of an icon (e.g., button) denoting a rejection of all but the marked (i.e., use selected) fragments. It is noted that in many cases, the user may not select any of the subset of simultaneously presented fragments for exclusion, when the search engine has high accuracy of retrieval, optionally when the search engine is iteratively updated as described herein. In such a case, the single gesture is the user providing an indication (e.g., clicking on an icon) indicating selection of all of the presented fragments. In another example, the user may press the Shift or Ctrl keys on the keyboard to indicate multiple selections, and make the multiple selections by clicking on multiple fragments. Letting go of the Shift or Ctrl key may denote completion of the selection. Alternatively, more than a single gesture may occur, for example, two (or more) gesture, such as a gesture per selected fragment, and another gesture to indicate completion of the selection.

Optionally, once a single selection is performed, the presentation is dismissed. Another set of fragments may be presented, as described herein. Alternatively, once one or more selections are made, another indication (e.g., another click) is provided to denote that the selection process has ended and another set may be presented.

At 112, at least some of the unclassified unstructured text fragments are classified into the medical classification term according to the selection by the user. The text fragments which are not classified may remain unclassified, or explicitly designated as unclassified.

In one implementation, non-selected unclassified unstructured text fragments are classified according to the medical classification term, and selected unclassified unstructured text fragments may be classified as not satisfying the medical classification term (e.g., remain unclassified, or are assigned a label that excludes classification by the medical classification term). In an alternative implementation, selected unclassified unstructured text fragments are classified according to the medical classification term. Non-selected unclassified unstructured text fragments may be classified as not satisfying the medical classification term.

Optionally, all instances of the unclassified unstructured text fragments in a corpus of the unstructured patient data are classified according to the respective medical classification term. The classification may be performed during each iteration. In a next iteration, text fragments which have been previously presented are not re-presented, which reduces workload of the user by the computer removing "doubles".

At 114, the features described with reference to one or more of 106-112 are iterated. During each iteration a new set of fragments are presented, selected, and/or classified. The iterations may be performed until no new previously unpresented unclassified unstructured text fragments are obtained by the search engine. Alternatively, the iterations may be performed until a stop condition is met, for example, a number (optionally predefined) of presented subsets of unclassified unstructured text fragments where the user does not provide an indication that any extracted fragments are incorrect, for example, where the search engine is dynamically updated after each iteration with the results of the user selection. In such a case, after the predefined number of subsets are determined to be correctly extracted, the search engine has converged to a high accuracy and may be assumed to be sufficiently correct for automatically annotating the rest of the unstructured patient data.

Optionally, the search engine is a trained model that is trained on a training dataset of labelled data using a supervised learning approach, i.e., text fragments labelled with one or more medical classification terms. The trained search engine may be updated during each iteration by being fed an indication of the classified and/or unclassified unstructured text fragments generated from the user selection. The trained search engine iteratively improves its ability to correctly extract text fragments based on the iterative updating using the user selections, which are considered as ground truth. The trained search engine may be implemented, for example, as a statistical classifier, such as a neural network. support vector machine (SVM), and/or random forest based model.

Optionally, each iteratively presented subset is obtained by executing the search engine (the same, or the updated trained model) on another sample portion of the unstructured patient data. During each iteration, the search engine extracts unique unclassified unstructured text fragments that have not been extracted in a previous iteration. Searching sample by sample may reduce computation time, especially when the unstructured patient data is very large, since repeated searches of the entire corpus is not necessarily required. Searching sample by sample may improve accuracy of the searches, such as when the search engine is iteratively updated. The accuracy of the updated search engine may incrementally improve during each iteration.

At 116, the annotated structured dataset is created and/or updated by the classification of unclassified unstructured text fragments into the medical classification term, i.e., according to the user selection or non-selected based on the implementation. The annotated structured dataset may be a newly created dataset (e.g., table) that maps medical classification terms to text fragments, or may be a mapping dataset that maps existing text fragments of the unstructured data to corresponding medical classification terms (e.g., set of pointers).

At 118, when the medical classification term is a single medical classification term selected from multiple medical classification terms, features 104-116 are iterated for each of the medical classification terms, optionally one medical classification term per iteration.

The annotated dataset is created to include multiple medical classification terms that classify the unstructured data fragments of the patient data. It is noted that each fragment may be classified into one or more terms.

At 120, the annotated dataset may be used, for example, to train an artificial intelligence model such as for automatic extraction of structured data from unstructured data, to serve as a ground truth for fully automatic systems for clinical data annotation, and/or for discrepancies detection in clinical records (e.g., annotated information is different from structured information attached to the clinical records).

Figure 3:
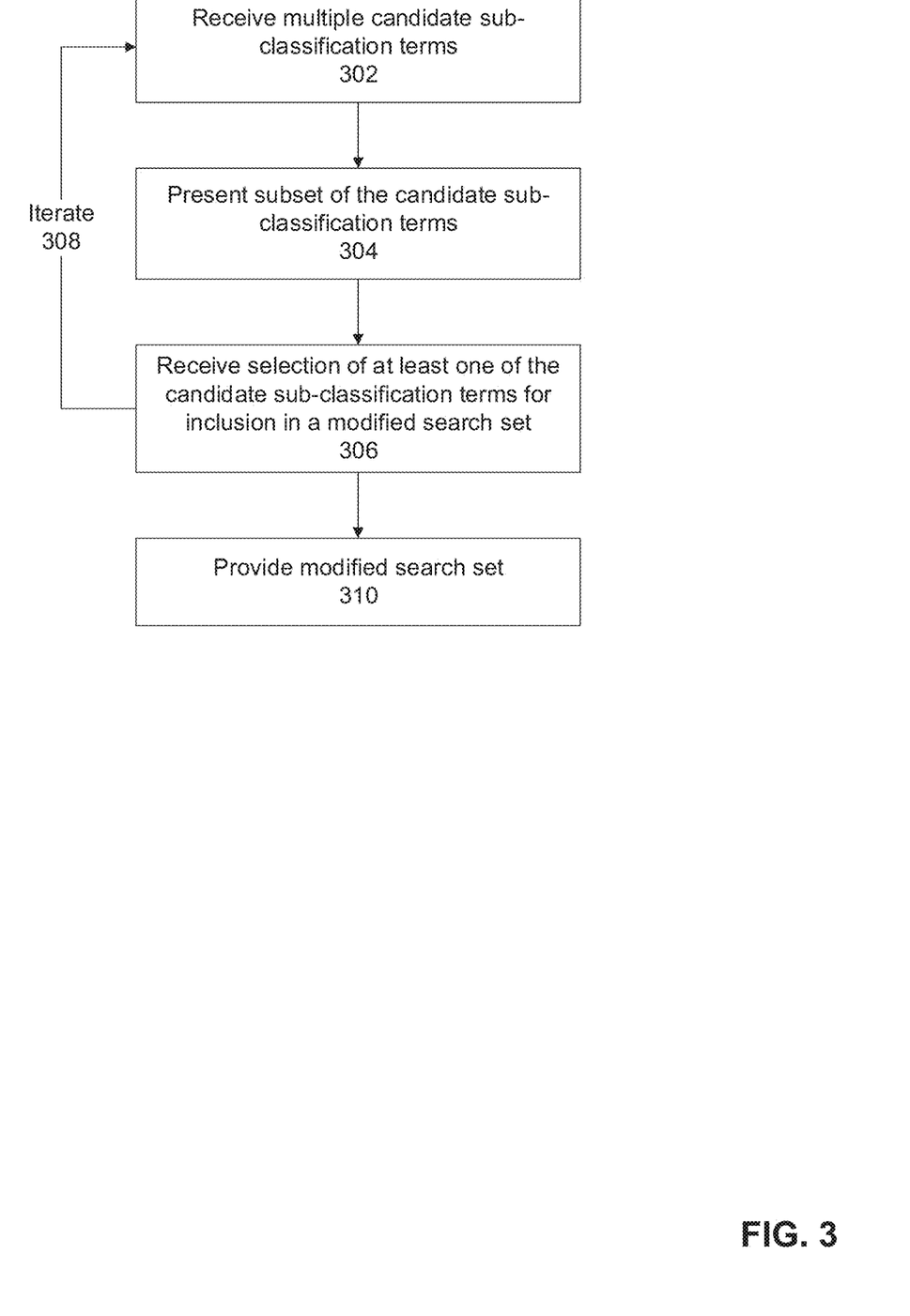
FIG. 3 is a flowchart of an exemplary process for creating a search set for searching by a search engine for extraction of unstructured unclassified text fragments, in accordance with some embodiments of the present invention.

Reference is now made to FIG. 3, which is a flowchart of an exemplary process for creating a search set for searching by a search engine for extraction of unstructured unclassified text fragments, in accordance with some embodiments of the present invention.

At 302, multiple candidate sub-classification terms are obtained. The multiple candidate terms are potentially semantically related to the medical classification term.

The candidate sub-classification terms may be extracted from unstructured data (e.g., the patient data, and/or other clinical data) by natural language processes (NLP) that are designed and trained to extract terms and phrases that are synthetically similar to an input term or phrase. For example, by an NLP model that is fed the medical classification term and searches over data to obtain the candidate sub-classification terms. In another example, using UMLS terms that correspond to the medical classification term.

At 304, a subset of the candidate sub-classification terms is presented on a display. The number of terms may be defined, for example, as described with reference to the number of the subset in 108 of FIG. 1. The presentation of the terms may be, for example, as described with reference to the presentation of the subset as in 108 of FIG. 1.

At 306, a selection of at least one of the candidate sub-classification terms is received from the user.

The selection may be for inclusion in a modified search set. Alternatively, the selection may be for exclusion from the modified search set.

The selection may be, for example, as described with reference to selection of members of the subset in 110 of FIG. 1, for example, using a single gesture within a GUI presenting the subset of candidate sub-classification terms.

At 308, features 302-306 may be iterated until all of the candidate sub-classification terms have been obtained, presented, and selections are made.

At 310, the modified search set is provided to the search engine for searching over at least a sample portion of the unstructured patient data using the modified search set, as described with reference to 106 of FIG. 1.

Figure 4:
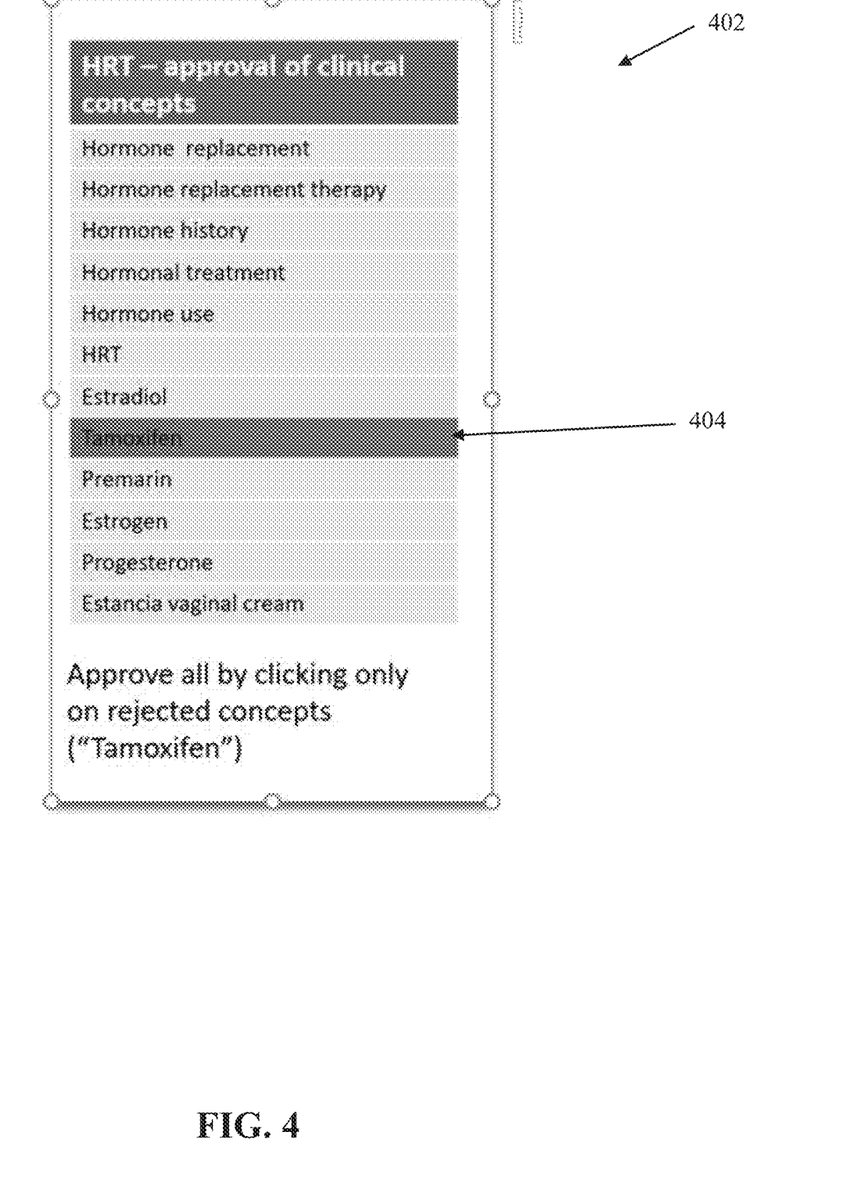
FIG. 4 is a schematic of an exemplary user interface for creating a search set for searching by a search engine for extraction of unstructured unclassified text fragments, in accordance with some embodiments of the present invention.

Reference is now made to FIG. 4, which is a schematic of an exemplary user interface 402 (e.g., GUI) for creating a search set for searching by a search engine for extraction of unstructured unclassified text fragments, in accordance with some embodiments of the present invention. UI 402 presents a list of candidate sub-classification terms for the medical classification term "hormone replacement therapy" (HRT). A user selects the term "Tamoxifen" for exclusion, for example, by clicking on the term and/or within the cell that the term is located in. The term may be highlighted to indicate the selection. The modified search set is created using the remaining, non-selected sub-classification terms.

Figure 5:
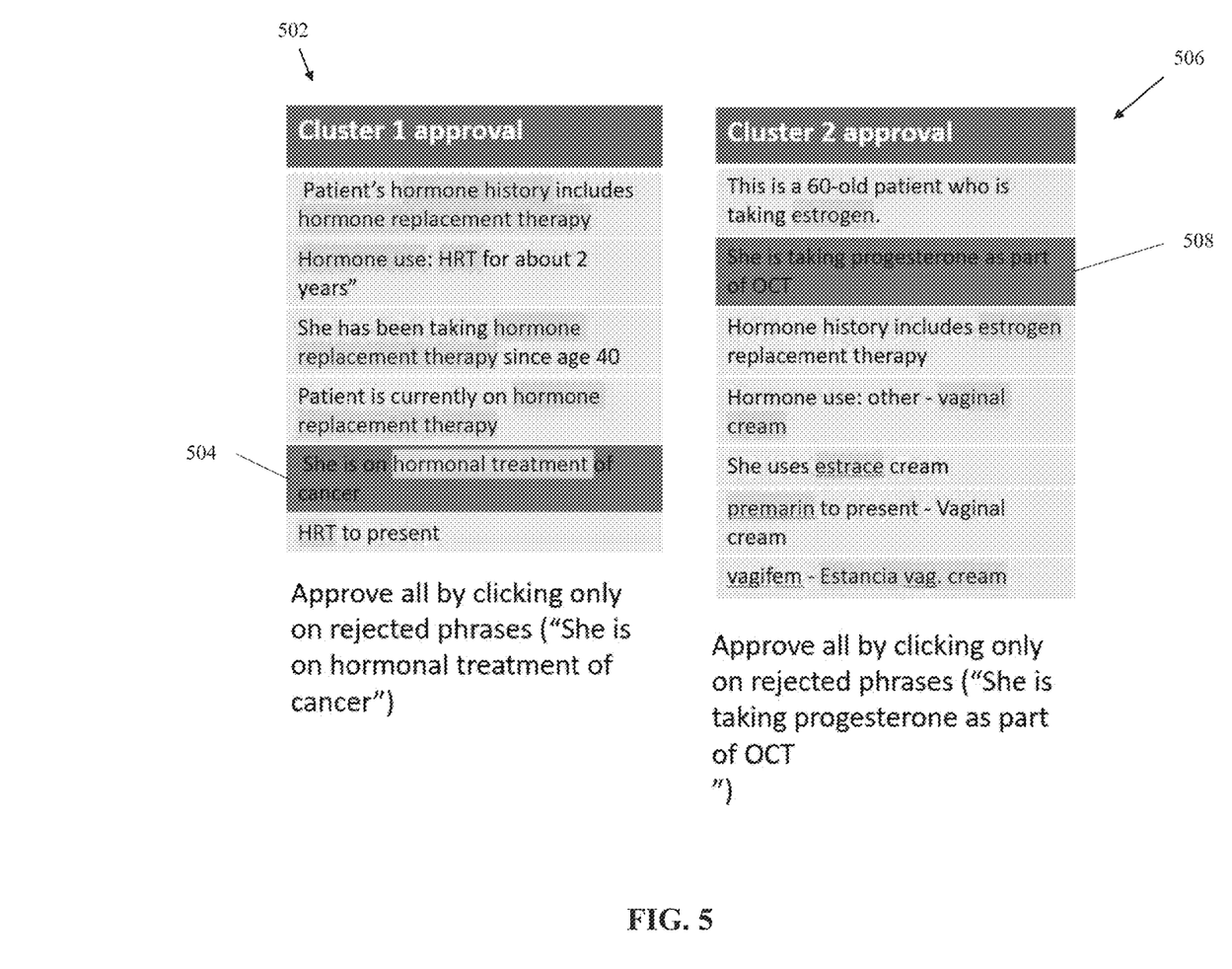
FIG. 5 is an exemplary user interface for generating an annotated dataset, in accordance with some embodiments of the present invention.

Reference is now made to FIG. 5, which is an exemplary user interface (e.g., GUI) for generating an annotated dataset, in accordance with some embodiments of the present invention. Interface 502 is presented in response to unclassified unstructured text fragments obtained by a search engine searching over unstructured patient data using the term "Hormone replacement therapy (HRT)". The search may be performed using the term HRT, and/or using the modified search set created using the user interface described with reference to FIG. 4.

A first subset of the fragments is presented in a presentation 502. The user selects the sentence fragment(s) which is/are incorrect, i.e., unrelated to HRT. As shown, the user selected the phrase "She is on hormonal treatment of cancer" 504, which is NOT to be classified under the medical classification term HRT. The user may perform the selection of 504, for example, by clicking on the term and/or within the cell that the term is located in. The term may be highlighted to indicate the selection. The non-selected fragments are classified according to the medical classification term HRT, and are used to create the annotated dataset, as described herein.

A second subset of the fragments are presented in an updated presentation 506. The second subset is obtained as described herein, for example, using a trained search engine that is updated with the results of the selection for the first subset, and/or searching on another portion of the unstructured patient dataset, and/or presenting additional fragments not previously presented. The user again selects the sentence fragment(s) which is/are incorrect, i.e., unrelated to HRT. As shown, the user selected the phrase "She is taking progesterone as part of OCT" 508, which is NOT to be classified under the medical classification term HRT. The user may perform the selection of 508, for example, by clicking on the term and/or within the cell that the term is located in. The term may be highlighted to indicate the selection. The non-selected fragments are classified according to the medical classification term HRT, and are used to create the annotated dataset, as described herein.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant unstructured data will be developed and the scope of the term unstructured data is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for generating an annotated structured dataset from unstructured patient data of a plurality of patients, comprising:
   at least one hardware processor executing a code for:
      receiving a medical classification term for classification of the unstructured patient data;
      searching, via a search engine, over a sample of the unstructured patient data using the medical classification term, for extracting a plurality of unclassified unstructured text fragments;
      presenting on a display, a subset of the plurality of unclassified unstructured text fragments;
      receiving from a user, an indication of a selection of none or at least one of the plurality of unclassified unstructured text fragments, and one of:
         (i) classifying as related to the medical classification term, non-selected unclassified unstructured text fragments according to the medical classification term, and for the selected unclassified unstructured text fragments which are identified by the selection as not related to the medical classification term, conducting at least one of: assigning the selected unclassified unstructured text fragments a label which excludes classification by the medical classification term and leaving the selected unclassified unstructured text fragments unclassified, and
         (ii) classifying as related to the medical classification term, selected unclassified unstructured text fragments according to the medical classification term, and for the non-selected unclassified unstructured text fragments which are identified by not being selected as not related to the medical classification term, conducting at least one of: assigning the non-selected unclassified unstructured text fragments a label which excludes classification by the medical classification term and leaving the non-selected unclassified unstructured text fragments unclassified; and
      iterating the searching, or the presenting of the subset, until no unclassified unstructured text fragments are obtained by the search engine,
      wherein the annotated structured dataset is created by the classification of unclassified unstructured text fragments into the medical classification term.

2. The system of claim 1, wherein the selection of the indication of at least one of the subset of the plurality of unstructured text fragments for exclusion or inclusion is performed using a single click, via a GUI presenting the subset of the plurality of unclassified unstructured text fragments.

3. The system of claim 1, wherein the search engine comprises a trained model trained on a training dataset of labeled data, and the trained search engine is updated during each iteration by being fed an indication of the plurality of classified or unclassified unstructured text fragments.

4. The system of claim 1, wherein each iteratively presented subset is obtained by executing the search engine on another sample of the unstructured patient data.

5. The system of claim 1, wherein during each iteration, the search engine extracts unique unclassified unstructured text fragments that have not been extracted in a previous iteration.

6. The system of claim 1, wherein during each iteration, all instances of the unclassified unstructured text fragments in a corpus of the unstructured patient data are classified according to the respective medical classification term.

7. The system of claim 1, further comprising:
   obtaining a plurality of candidate sub-classification terms potentially semantically related to the medical classification term, presenting on a display, a subset of the plurality of candidate sub-classification terms, receiving, from a user, a selection of at least one of the plurality of candidate sub-classification terms for inclusion in a modified search set;

iterating the obtaining or the presenting until all of the plurality of candidate sub-classification terms have been obtained and presented, and wherein the search engine searches over the sample of the unstructured patient data using the modified search set.

8. The system of claim 7, wherein the selection of the at least one of the plurality of candidate sub-classification terms is for exclusion from the modified search set, and is performed using a single click, via a GUI presenting the cluster of the subset of the plurality of candidate sub-classification terms.

9. The system of claim 7, wherein the plurality of candidate sub classification terms are extracted from unstructured clinical data by natural language processes (NLP) that are designed and trained to extract terms and phrases that are synthetically similar to an input term or phrase.

10. The system of claim 1, wherein the unstructured patient data includes at least one member of the group consisting of: physician manually written notes, and transcribed dictations.

11. The system of claim 1, wherein the unstructured patient data is created by a plurality of different healthcare providers using different terminology that has a semantically similar meaning.

12. The system of claim 1, wherein a number of members of the subset of the plurality of unclassified unstructured text fragments simultaneously respectively presented within a GUI is selected according to screen parameters of a display presenting the GUI.

13. The system of claim 1, further comprising selecting the subset of the plurality of unclassified unstructured text fragments for presentation according to a statistical similarity value, wherein unclassified unstructured text fragments of the subset have a higher statistical similar value in comparison to non-selected unclassified unstructured text fragments excluded from the subset.

14. The system of claim 1, further comprising selecting the subset of the plurality of unclassified unstructured text fragments of a current iteration according to a statistical similarity value computed relative to unclassified unstructured text fragments selected from the subset of a previous iteration.

15. The system of claim 14, wherein the subset is selected according to a requirement of the statistical similarity value denoting similarity to the previous iteration.

16. The system of claim 14, wherein the subset is selected according to a requirement of the statistical similarity value denoting dis-similarity to at least one indication of the subset of the plurality of unclassified unstructured text fragments selected for exclusion in a previous iteration.

17. The system of claim 1, wherein the medical classification term is based on clinical data, and the unstructured patient data is of medical records of the patients.

18. The system of claim 1, wherein the medical classification term is one medical classification term selected from a plurality of medical classification terms, and the code is iterated for each of the plurality of medical classification terms, and wherein the annotated dataset includes at least one of the plurality of medical classification terms classifying unstructured data fragments of patient data for each of the plurality of patients.

19. A method of generating an annotated structured dataset from unstructured patient data of a plurality of patients, comprising:

receiving a medical classification term for classification of the unstructured patient data;

searching, via a search engine, over a sample of the unstructured patient data using the medical classification term, for extracting a plurality of unclassified unstructured text fragments;

presenting on a display, a subset of the plurality of unclassified unstructured text fragments;

receiving from a user, an indication of a selection of none or at least one of the plurality of unclassified unstructured text fragments, and one of:

(i) classifying as related to the medical classification term, non-selected unclassified unstructured text fragments according to the medical classification term, and for the selected unclassified unstructured text fragments which are identified by the selection as not related to the medical classification term, conducting at least one of: assigning the selected unclassified unstructured text fragments a label which excludes classification by the medical classification term and leaving the selected unclassified unstructured text fragments unclassified, and (ii) classifying as related to the medical classification term, selected unclassified unstructured text fragments according to the medical classification term, and for the non-selected unclassified unstructured text fragments which are identified by not being selected as not related to the medical classification term, conducting at least one of: assigning the non-selected unclassified unstructured text fragments a label which excludes classification by the medical classification term, and leaving the non-selected unclassified unstructured text fragments unclassified; and iterating the searching, or the presenting of the subset, until no unclassified unstructured text fragments are obtained by the search engine, wherein the annotated structured dataset is created by the classification of unclassified unstructured text fragments into the medical classification term.

20. A computer program product for generating an annotated structured dataset from unstructured patient data of a plurality of patients, comprising:

a non-transitory memory storing thereon code for execution by at least one hardware process, the code including instructions for:

receiving a medical classification term for classification of the unstructured patient data;

searching, via a search engine, over a sample of the unstructured patient data using the medical classification term, for extracting a plurality of unclassified unstructured text fragments;

presenting on a display, a subset of the plurality of unclassified unstructured text fragments;

receiving from a user, an indication of a selection of none or at least one of the plurality of unclassified unstructured text fragments, and one of:

(i) classifying as related to the medical classification term, non-selected unclassified unstructured text fragments according to the medical classification term, and for the selected unclassified unstructured text fragments which are identified by the selection as not related to the medical classification term, conducting at least one of: assigning the selected unclassified unstructured text fragments a label which excludes classification by the medical classification term and leaving the selected unclassified unstructured text fragments unclassified, and (ii) classifying as related to the medical classification term, selected unclassified unstructured text fragments according to the medical classification term, and for the non-selected unclassified unstructured text fragments which are identified by not being selected as not related to the medical classification term, conducting at least one of: assigning the selected unclassified unstructured text fragments a label which excludes classification by the medical classification term and leaving the non-selected unclassified unstructured text fragments unclassified; and iterating the searching, or the presenting of the subset, until no unclassified unstructured text fragments are obtained by the search engine, wherein the annotated structured dataset is created by the classification of unclassified unstructured text fragments into the medical classification term.

\* \* \* \* \*